(12) United States Patent
Uchida et al.

(10) Patent No.: US 6,432,289 B1
(45) Date of Patent: Aug. 13, 2002

(54) OXYGEN CONCENTRATION DETECTOR

(75) Inventors: Yasuhiro Uchida; Takashi Kojima; Masahiro Hamaya; Minoru Ota, all of Kariya (JP)

(73) Assignee: Denso Corporation (JP)

(*) Notice: Subject to any disclaimer, the term of this patent is extended or adjusted under 35 U.S.C. 154(b) by 1052 days.

(21) Appl. No.: 08/593,330

(22) Filed: Jan. 31, 1996

(30) Foreign Application Priority Data

Feb. 1, 1995 (JP) .............................................. 7-037591
Dec. 27, 1995 (JP) .............................................. 7-354505

(51) Int. Cl.[7] .......................................... G01N 27/407
(52) U.S. Cl. ........................ 204/428; 204/408; 205/784
(58) Field of Search ................. 204/421–429; 205/783.5, 784, 784.5, 785

(56) References Cited

U.S. PATENT DOCUMENTS

| | | | | |
|---|---|---|---|---|
| 3,598,711 A | * | 8/1971 | Plais | 204/427 |
| 3,915,828 A | * | 10/1975 | Cleary et al. | 204/427 |
| 4,505,807 A | * | 3/1985 | Yamada | 204/426 |
| 4,512,871 A | * | 4/1985 | Kato et al. | 204/428 |
| 4,569,748 A | * | 2/1986 | Yamakawa et al. | 204/429 |
| 4,591,423 A | * | 5/1986 | Kato et al. | 204/428 |
| 4,624,770 A | * | 11/1986 | Yamada et al. | 204/428 |
| 4,756,885 A | * | 7/1988 | Raff et al. | 204/428 |
| 5,164,068 A | * | 11/1992 | Udo et al. | 204/428 |

FOREIGN PATENT DOCUMENTS

JP          63-180848          7/1988

* cited by examiner

Primary Examiner—T. Tung
(74) Attorney, Agent, or Firm—Nixon & Vanderhye PC

(57) ABSTRACT

An oxygen concentration detector comprises a solid electrolyte 21, a sensing element 2 which consists of the solid electrolyte 21 coated on the surface with an outer electrode 23, a heater 3 provided inside the solid electrolyte 21, and a protecting cover 16 which protects the sensing element 2. The protecting cover 16 has two levels of openings 161, 162, the outer electrode 23 is constructed within the range defined by the length of the heat-generating part 31 of the heater 3, and the relationship between the length $L_1$ of the heat-generating part 31 and the distance between the openings $L_2$ of the two levels of openings 161, 162 in the axial direction is such that $L_1/L_2=0.9$ to $1.3$.

11 Claims, 13 Drawing Sheets

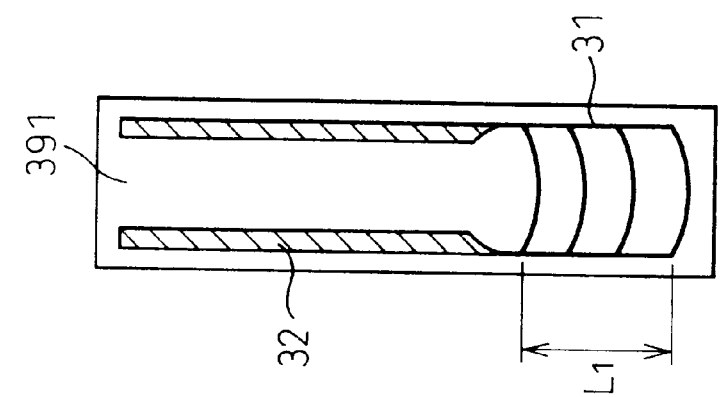
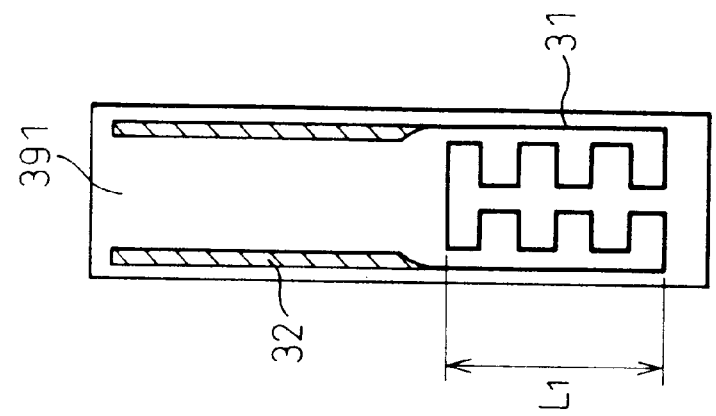
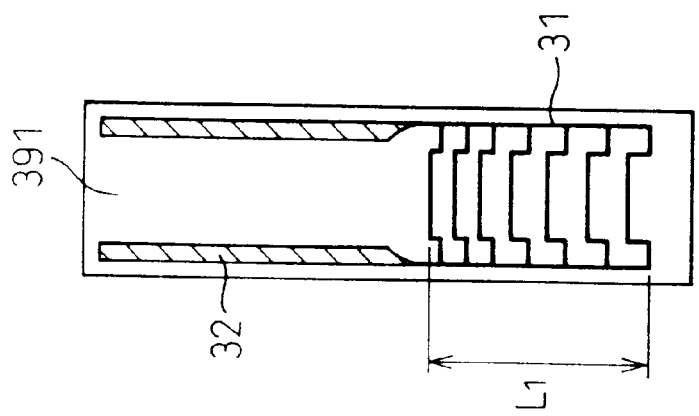

OXYGEN CONCENTRATION DETECTOR

BACKGROUND OF THE INVENTION

1. Field of the Invention

The present invention relates to an oxygen concentration detector which is used for air/fuel ratio control, etc. in an automobile engine.

2. Description of the Related Art

Oxygen concentration detectors have conventionally been provided with protecting covers to protect their sensing elements. That is, an oxygen concentration detector has a solid electrolyte, a sensing element which consists of the solid electrolyte coated on the surface with an outer electrode, a heater provided inside the above-mentioned solid electrolyte, and a protecting cover which protects the above-mentioned sensing element. In addition, two levels of openings are provided in the above-mentioned protecting cover, through which a gas to be measured is introduced into the gas-measuring chamber.

The oxygen concentration detector described above is sometimes mounted onto the exhaust pipe, etc. and used as a part of the engine's combustion control system, in order to make the automobile engine burn fuel at the theoretical air/fuel ratio. The exhaust gas cleaning efficiency is highest when the engine burns fuel at the theoretical air/fuel ratio.

However, in order to further increase the exhaust gas cleaning efficiency, it has been attempted, in recent years, to raise the sensitivity of the oxygen concentration detectors used for detecting the air/fuel ratio.

The sensing elements of such oxygen concentration detectors, however, have unstable characteristics until heated above the activation temperature. As a result, when the temperature of the sensing element is low, for example, when the engine is started, the oxygen concentration sensitivity is also low.

Consequently, in order to increase the exhaust gas cleaning efficiency, it is necessary to heat the sensing element to the above-mentioned activation temperature within a short time after starting the engine.

To meet this requirement, it has been proposed to heat the sensing element by increasing the power fed to the heater to increase the heater temperature.

However, in such cases there is a risk that the temperature of the heat-generating part inside the heater may increase to an abnormally high temperature which is considerably higher than the temperature necessary for oxygen concentration detection, and may even rise above the heat-resistant temperature of the ceramic or other material of which the heater is constructed. This results in problems such as damage to the heater and the shortening of its useable life.

In light of these problems, it is an object of the present invention to provide an oxygen concentration sensing element which allows the sensing element to be heated to the activation temperature more rapidly, without raising the temperature of the heat-generating part above the heat-resistant temperature of the heater.

SUMMARY OF THE INVENTION

The present invention is an oxygen concentration detector which comprises a sensing element which includes a solid electrolyte coated on the surface thereof with an outer electrode, a heater provided inside or near the above-mentioned solid electrolyte, and a protecting cover which protects the above-mentioned sensing element, characterized in that the protecting cover has two levels of openings, and
the area of the outer electrode which contributes to the exchange (conduction) of oxygen ions is constructed within the range defined by the length of the heat-generating part of the heater, and the section of the protecting cover adjacent (nearest) to the sensing element is provided with two levels of openings in the axial direction outside the range corresponding to the range in which the outer electrode contributes to exchange of oxygen ions, wherein the relationship between the length $L_1$ of the heat-generating part and the distance between the openings $L_2$ of the two levels of openings in the axial direction is such that $L_1/L_2 = 0.9–1.3$.

The above-mentioned two levels of openings may be coaxial with respect to the central axis of the oxygen concentration detector, or they may be non-coaxial, at spirally offset positions. The distance between the two levels of openings is the distance from the perimeter line including the lower edge of the openings at the proximal end of the sensing element to the perimeter line including the upper edge of the openings at the distal end of the sensing element (see FIGS. 7(A), (B)).

The heater consists of a heat-generating part which increases in temperature upon electrification to heat the sensing element, a lead part which supplies power to the heat-generating part, and a ceramic body which houses the heat-generating part and the lead part. The heat-generating part and the lead part may take any of a variety of shapes (see FIG. 8, FIGS. 15–18), and the construction of the present invention may be applied to heat-generating parts and lead parts of all such shapes.

The heat-generating part is made of a paste consisting of, for example, platinum, tungsten, molybdenum or the like. Furthermore, the heater may either be provided inside the sensing element as a separate heater, or it may be formed integrally with the solid electrolyte of the sensing element (which results in a layered sensing element).

The relationship between the length $L_1$ of the heat-generating part and the distance between the openings $L_2$ is such that $L_1/L_2=0.9–1.3$. If the value of $L_1/L_2$ is less than 0.9, then there is a possibility that the temperature of the heat-generating part may rise above the heat-resistant temperature of the heater when the sensing element is heated to the activation temperature. This may result in damage to the heater and the shortening of its useable life.

On the other hand, if the value exceeds 1.3 the power consumption of the heat-generating part may increase, thus lowering efficiency.

A lower power consumption is also preferred since the heater has a positive resistance temperature coefficient, and thus in cases where the heater resistance is high, sufficient power sometimes may not be provided by the voltage of the battery mounted in the automobile.

The length of the heat-generating part is preferably between 8 mm and 16 mm. If the length is less than 8 mm, then the temperature of the heat-generating part may rise above the heat-resistant temperature of the heater when the sensing element is heated to the activation temperature. Conversely, a length exceeding 16 mm will increase power consumption by the heat-generating part and may result in the same type of problem as when the value of $L_1/L_2$ is greater than 1.3.

The distance between the openings $L_2$ is preferably between 9 mm and 16 mm. If the length is less than 9 mm, then the shorter distance between the outer electrode of the sensing element and the openings may result in a greater tendency toward deterioration of the outer electrode due to contamination in the gas to be measured. Conversely, if the length exceeds 16 mm then the longer distance between the outer electrode of the sensing element and the openings may result in a poor response.

The axial offset ΔL between the center position of the heat-generating part of the heater and the center position of the distance between the openings $L_2$. is preferably no more than $L_2/4$.

If this ΔL is longer than $L_2/4$, as explained below, the sensing element will be cooled by the low-temperature gas to be measured which is introduced through the openings, and this may make it impossible to rapidly heat the sensing element to the activation temperature.

The area of the individual openings in the openings is preferably between 0.75 and 3.5 $mm^2$, and the total area counting both levels of openings is preferably between 10 and 23 $mm^2$. If the total area of both levels of openings is less than 10 $mm^2$, then it may become impossible to introduce a sufficient amount of the gas to be measured into the gas-measuring chamber to allow detection of the oxygen concentration, and if the area of each individual opening is less than 0.75 $mm^2$, then working of the openings becomes problematic, resulting in disadvantages from the viewpoints of workability and productivity.

Conversely, if the total area of the openings of both levels is greater than 23 $mm^2$, then cooling of the sensing element when the low-temperature gas to be measured is introduced may render it impossible to reach the activation temperature without excessively raising the temperature of the heat-generating part. If the area of each opening is greater than 3.5 $mm^2$, condensed water in the exhaust gas pipe may pass through the opening so that the element is damaged or cracked by contact of water.

The above-mentioned outer electrode is provided as a band around the surface of the solid electrolyte, and the outer electrode preferably does not face the openings of the above-mentioned protecting cover.

That is, most limiting current-type oxygen concentration detectors have the outer electrode on only specific sections of the sensing element. Also, since the outer electrode is the most essential part for oxygen concentration detection, this section must be kept at the activation temperature for stable detection of the oxygen concentration.

Consequently, situating the above-mentioned openings and outer electrode in the manner described above makes it possible to prevent lowering of the temperature of the outer electrode when the low-temperature gas to be measured is introduced. An additional effect is that since it is possible to avoid direct contact between the outer electrode and the gas to be measured which is introduced through the openings, there may be realized a reduction in electrode malfunction and loading of the diffusion layer due to toxins in the gas.

The surface of the outer electrode may also have a gas diffusion-resistant layer. Providing a limiting current-type oxygen concentration detector with such a gas diffusion-resistant layer will allow adjustment of the number of oxygen molecules and oxygen ions taken into the sensing element, to obtain the desired output.

The exterior of the above-mentioned protecting cover may be provided with an external cover which has through-holes. Water droplets infiltrating through the openings in the protecting cover cause water cracks in the sensing element, and contamination in the gas to be measured results in its deterioration. Thus, providing an external cover on the exterior of the protecting cover will effectively protect the sensing element from such damage. An opening may be provided at the bottom of the cover for the sensor element, which may improve the responsibility of the sensor.

In the oxygen concentration detector of the present invention, the section of the outer electrode of the sensing element which contributes to the exchange of oxygen ions is constructed within the area defined by the length of the heat-generating part of the heater.

As a result, the heat from the heater is received over the entire surface of the outer electrode. Thus, the heater is able to preferentially heat the sections most useful for detection of oxygen concentration, and thus heat the sensing element to the activation temperature without causing the temperature of the heat-generating part to rise above the heat-resistant temperature of the heater.

In addition, the specific relationship described above is set between the length $L_1$ of the heat-generating part and the distance between the openings $L_2$ of the two levels of openings in the axial direction.

This allows the sensing element to receive the heat from the heat-generating part in the most efficient manner. As a result, since the heater can heat the sensing element more efficiently, the sensing element may be heated to the activation temperature by a heater with a lower temperature.

The present invention is most effective when the temperature of the gas to be measured is considerably lower than the activation temperature of the sensing element.

Thus, according to the present invention there is provided an oxygen concentration detector which allows the sensing element to be heated to the activation temperature more rapidly, without raising the temperature of the heat-generating part above the heat-resistant temperature of the heater.

BRIEF DESCRIPTION OF THE DRAWINGS

FIGS. 16A to 16C illustrate different heat-generating parts for Example 4.

DESCRIPTION OF THE PREFERRED EMBODIMENTS

Example 1

An oxygen concentration detector 1 according to an example of the present invention will now be explained with reference to FIGS. 1 to 9.

Figure 1:
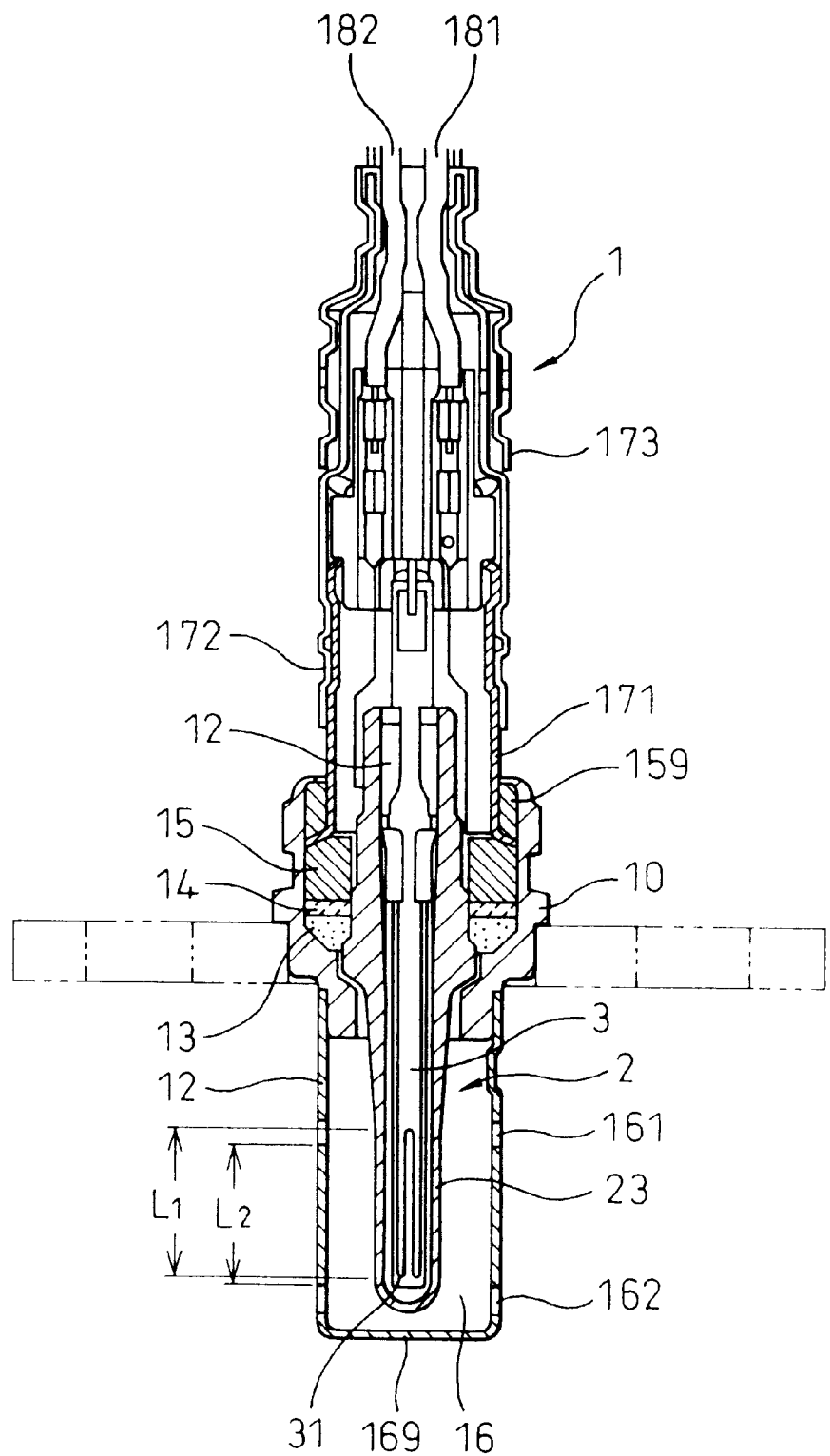
FIG. 1 is a cross-sectional view of an oxygen concentration detector for Example 1.

As shown in FIG. 1, the oxygen concentration detector 1 according to this embodiment comprises a solid electrolyte 21, a sensing element 2 which is composed of the solid electrolyte 21 partially coated on the surface with an outer electrode 23 (see FIG. 5), a heater 3 provided inside the sensing element 2, and a protecting cover 16 which protects the sensing element 2.

The protecting cover 16 has two levels of openings 161 and 162. The two levels of openings 161 and 162 are openings 161 at the proximal end of the sensing element and openings 162 at the distal end of the sensing element. Each of the openings 161, 162 comprise a plurality of openings in the protecting cover 16, and their respective centers are located so as to be aligned on the same perimeter line of the cross-sectionally circular protecting cover 16.

Figure 5:
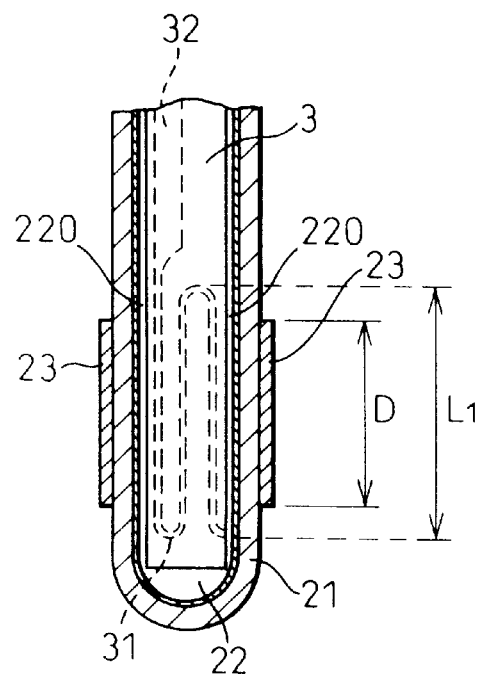
FIG. 5 is an abbreviated cross-sectional view of a sensing element for Example 1.

As shown in FIGS. 1 and 5, the outer electrode 23 is constructed within the range defined by the length $L_1$ of the heat-generating part 31 of the heater 3. That is, both the proximal and distal ends of the outer electrode 23 of width D are within the range of the heat-generating part 31.

Figure 2:
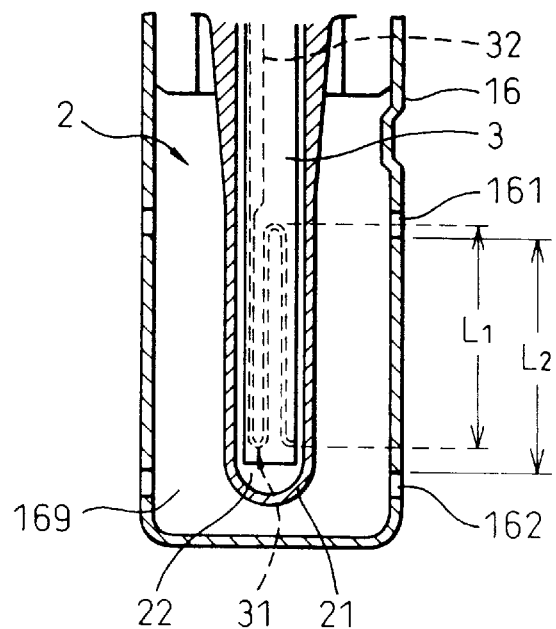
FIG. 2 is an abbreviated cross-sectional view of a sensing element and protecting cover for Example 1.

Also, as shown in FIG. 2, the relationship between the length $L_1$ of the heat-generating part 31 and the axial distance between the openings $L_2$ of the two levels of openings 161, 162 is such that $L_1/L_2 \leq 1.1$. The length $L_1$ of the heat-generating part 31 is 14.5 mm, and the distance between the openings $L_2$ is 13 mm. Also, the openings of both openings 161, 162 are circular with a diameter of 1.5 mm, and the total area of the openings is about 14 $mm_2$ (a total of 8 circular openings are provided, 4 equally spaced on each level).

Figure 7A:
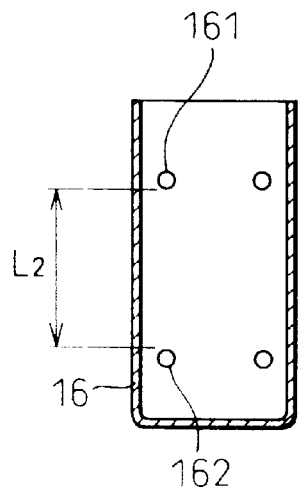
FIGS. 7A and 7B illustrate of two types of protecting covers for Example 1.
Figure 7B:
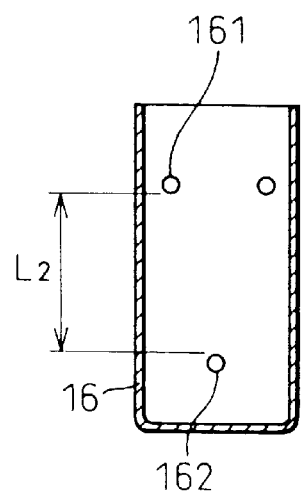
Figure 19:
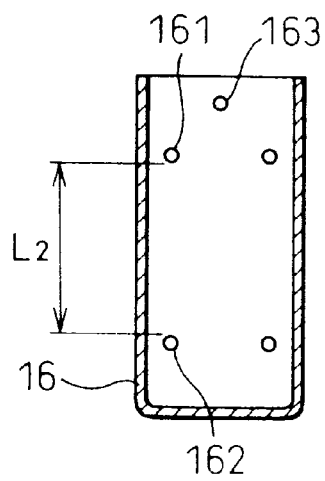
FIG. 19 illustrates a protecting cover for Example 5.

When, as shown in FIG. 7A, each of the openings 161, 162 lies on the same axis with respect to the axial direction of the oxygen concentration detector 1, the distance between the openings is the distance between the lower edges of each of the openings 161 at the proximal end of the sensing element and the upper edges of each of the openings 162 at the distal end of the sensing element. Alternatively, even if the axes are spirally offset as shown in FIG. 7B, it is still the distance between the upper and lower edges of the openings 161, 162 when measured in the vertical direction. As a further alternative to the configuration of the two levels of openings shown in FIGS. 7A and 7B, there may also be openings at sections offset from the axial direction of the two levels of openings, as shown in FIG. 19.

Figure 3:
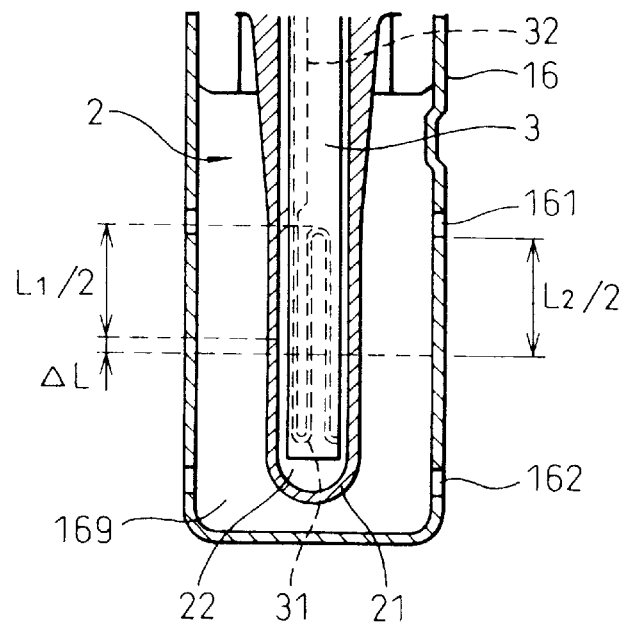
FIG. 3 is an abbreviated cross-sectional view of a sensing element and protecting cover for Example 1.

Also, as shown in FIG. 3, the axial offset ΔL between the center position of the heat-generating part 31 of the heater 3 and the center position of the distance between the openings is preferably no more than $L_2/4$.

As shown in FIGS. 1 and 5, the sensing element 2 of the oxygen concentration detector 1 comprises a test tube-shaped solid electrolyte 21 which has a standard gas chamber 22 provided with an inner electrode 220. The heater 3 is inserted and fixed in the standard gas chamber 22 using a fitting 12.

The sensing element 2, as shown in FIG. 1, is inserted into a metal housing 10 through an insulative ceramic insulator 15, packing 14 and talc powder 13. An external cover 17 is caulked with a ring 159 at the upper end of the housing 10.

As shown in FIG. 1, a protecting cover 16 is fixed at the lower end of the housing 10, and this protecting cover 16 forms a gas-measuring chamber 169 around the sensing element 2.

Figure 6:
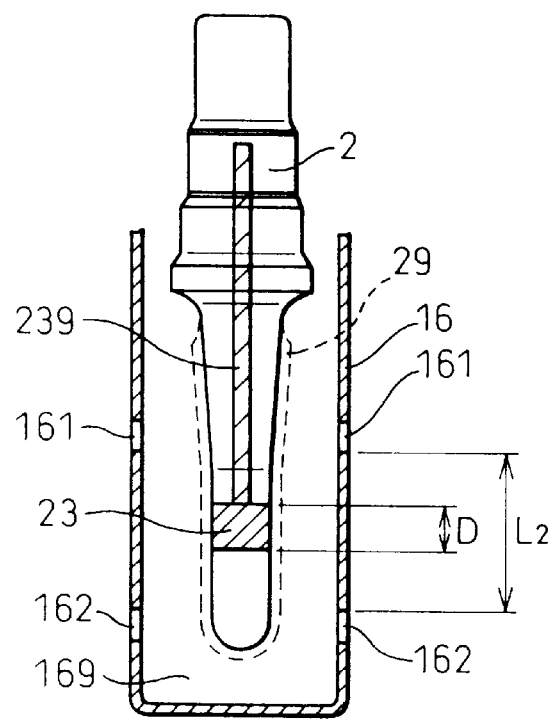
FIG. 6 is an abbreviated view of a sensing element and protecting cover for Example 1.

As shown in FIG. 6, the protecting cover 16 is provided so that the outer electrode 23 of width D is situated between the openings 161 at the proximal end of the sensing element and the openings 162 at the distal end of the sensing element.

In FIG. 1, the numerals 171, 172 and 173 denote external covers and the numerals 181 and 182 denote lead wires, while in FIG. 6 the numeral 29 denotes a gas diffusion-resistant layer and the numeral 239 denotes a lead part.

The lead part 239 reaches to the top to create a continuous connection between the outer electrode 23 and the lead terminal extending from the lead wire 181 (FIG. 6).

Figure 4:
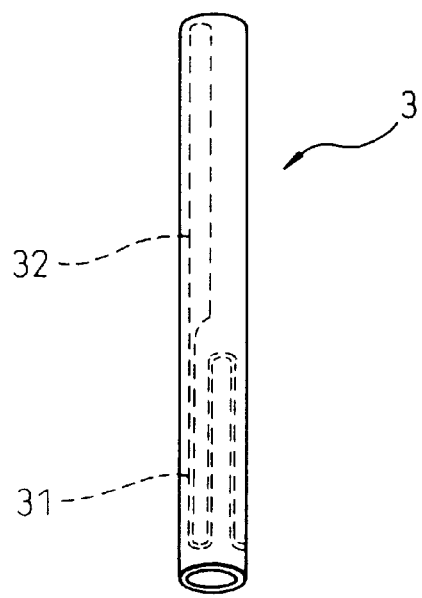
FIG. 4 is a perspective view of a heater for Example 1.

As shown in FIG. 4, the heater 3 is a cylinder made of ceramic, and the heat-generating part 31 and the lead part 32 are formed inside the outer shell.

Figure 8:
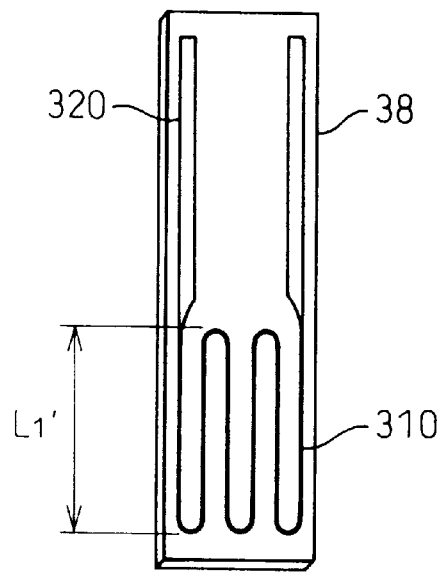
FIG. 8 illustrates a heat-generating part of a heater for Example 1.
Figure 9:
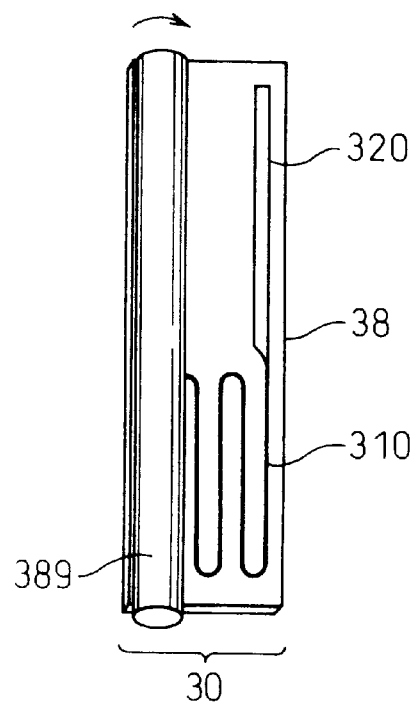
FIG. 9 illustrates a heat-generating part of a heater of Example 1.

As shown in FIG. 8, the heater 3 may be prepared by printing a tungsten paste on an unbaked ceramic sheet 38 and, as shown in FIG. 9, wrapping the ceramic sheet 38 around a heating ceramic rod 389 to create a ceramic body 30, and then baking the ceramic body 30.

In FIG. 8, the comb tooth-shaped patterned section 310 becomes the heat-generating part 31 upon baking, while the wide section 320 above the patterned section 310 becomes the lead part 32. Since the ceramic sheet 38 and the ceramic rod 389 contract upon baking, the length $L_1'$ of the patterned section 310 is slightly longer than $L_1$.

The effect of the present embodiment will now be explained.

In the oxygen concentration detector of this embodiment, the outer electrode 23 of the sensing element 2 is constructed within the range defined by the length of the heat-generating part 31 of the heater 3.

As a result, the heat from the heater 3 is received over the entire surface of the outer electrode 23, and thus the heater 3 is able to preferentially heat the sections most useful for detection of oxygen concentration. Consequently, it becomes possible to heat the sensing element 2 to the activation temperature without causing the temperature of the heat-generating part 31 to rise above the heat-resistant temperature of the heater 3.

In addition, the specific relationship described above is set between the length $L_1$ of the heat-generating part 31 and the distance between the openings $L_2$ of the two levels of openings 161, 162.

This allows the sensing element 2 to receive the heat from the heat-generating part 31 in the most efficient manner, and thus allows the heater 3 to heat the sensing element 2 more efficiently. This construction is particularly effective in cases where the temperature of the gas to be measured is considerably lower than the activation temperature of the sensing element 2.

Thus, according to this embodiment, there is provided an oxygen concentration detector which allows the sensing element to be heated to the activation temperature more rapidly, without raising the temperature of the heat-generating part above the heat-resistant temperature of the heater.

Furthermore, in this embodiment the openings 161, 162 and the outer electrode 23 are not facing each other. The outer electrode 23 is the part used for oxygen concentration detection. In this embodiment, therefore, it is possible to prevent lowering of the temperature of the outer electrode 23, and thus keep the outer electrode 23 at the activation temperature, even when low-temperature gas is introduced. In addition, since it is possible to avoid direct contact between the outer electrode and the gas to be measured, there may be realized a reduction in electrode malfunction and loading of the diffusion layer due to contamination in the gas.

Example 2

This embodiment, shown in FIGS. 10 to 13, illustrates the relationships between the ratio $L_1/L_2$ and $\Delta L$, and the heater temperature and heater power.

Figure 10:
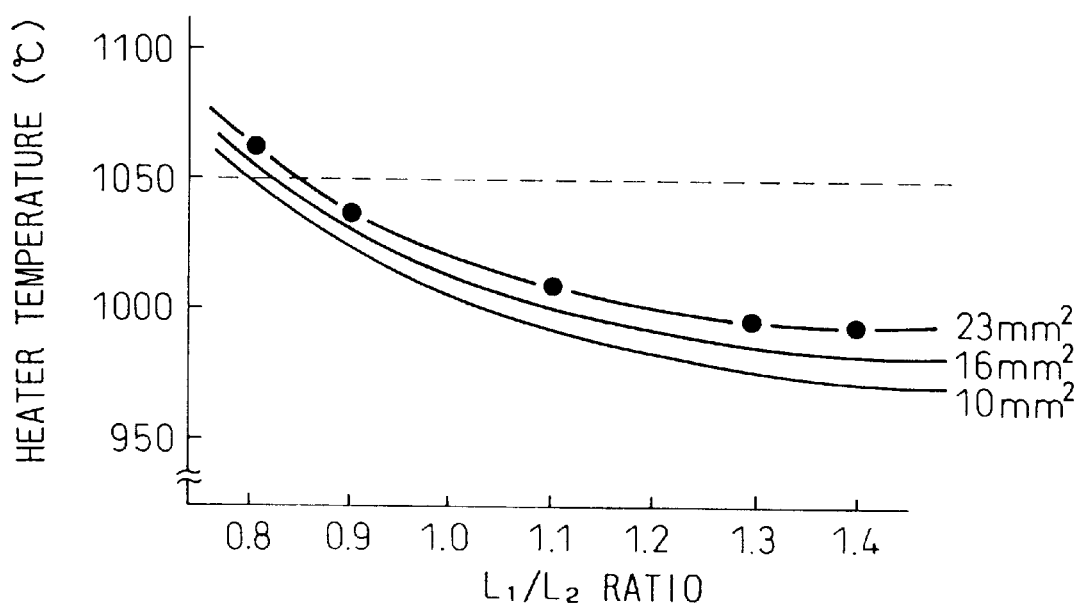
FIG. 10 is a graph showing the relationship between the ratio $L_1/L_2$ and the heater temperature for Example 2.
Figure 11:
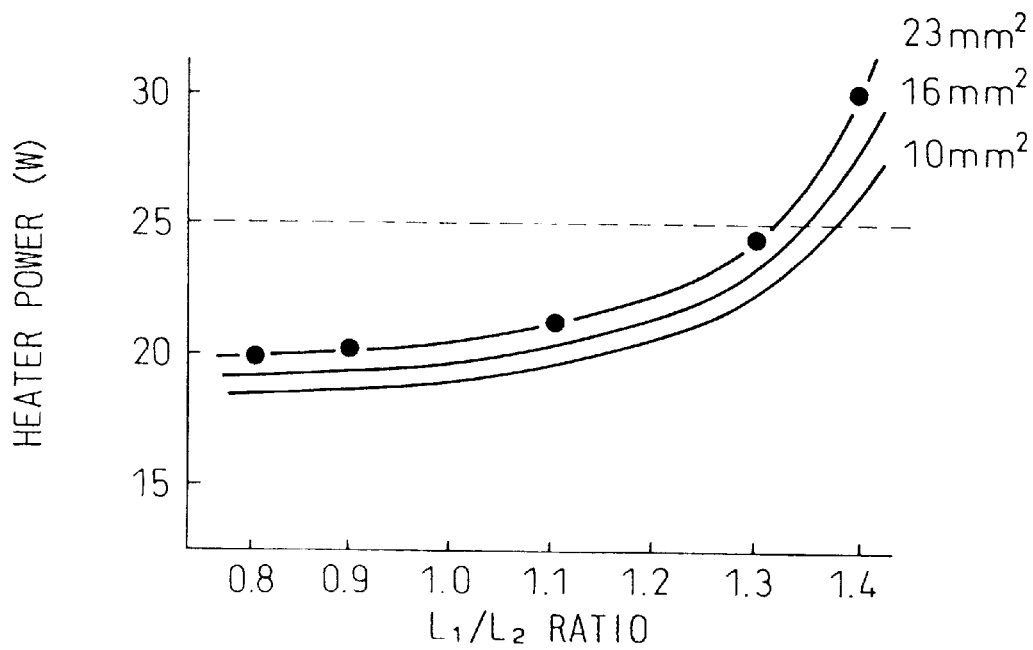
FIG. 11 is a graph showing the relationship between the ratio $L_1/L_2$ and the heater power for Example 2.

First, in the graphs of FIGS. 10 and 11, the x-axis represents the values of the ratio $L_1/L_2$. The y-axis represents the heater temperature and heater power at the time of measurement, as explained below.

In other words, in an oxygen concentration detector having the same construction as in Example 1, with a $\Delta L$ of 0 mm, the heater is electrified to heat the sensing element to a temperature of between 300° C. and 700° C. The heater temperature and required power at the time of this heating are measured while varying the ratio $L_1/L_2$. The parameters for the total area of the upper and lower levels of openings were 10, 16 and 23 mm².

The same graph shows that when $L_1/L_2$ is less than 0.9, the heater temperature increases drastically, exceeding 1050° C., the heat-resistant temperature of the heater.

On the other hand, when $L_1/L_2$ is greater than 1.3, the heater power increases to exceed 25 W, resulting in poor efficiency of the heater.

In addition, since the heater of this embodiment has a high resistance, when $L_1/L_2$ is greater than 1.3 it is no longer possible to supply sufficient power for the temperature increase with the voltage of a battery mounted in an automobile.

Figure 12:
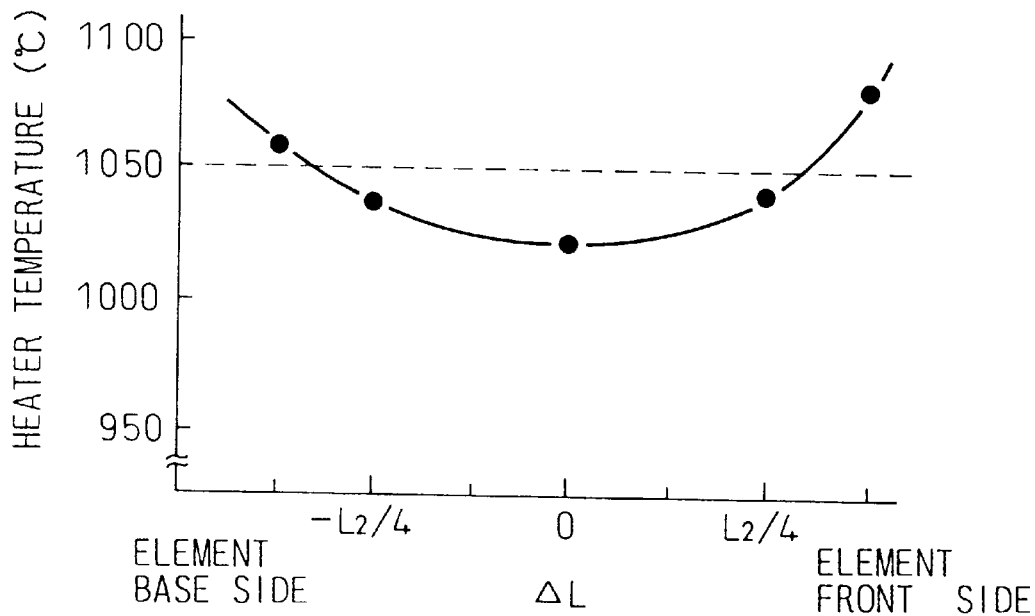
FIG. 12 is a graph showing the relationship between ΔL and the heater temperature for Example 2.
Figure 13:
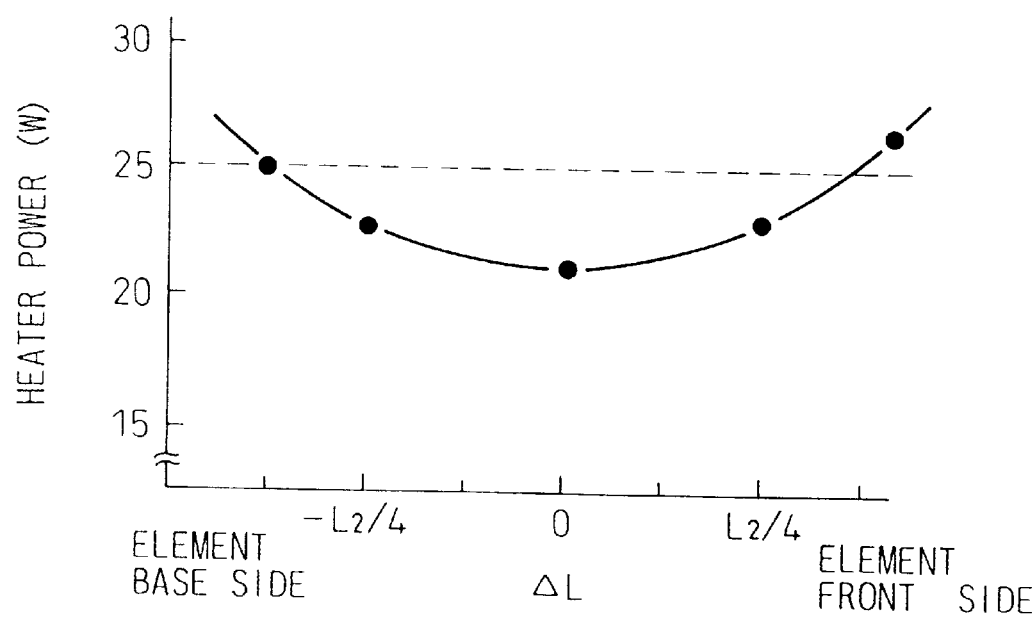
FIG. 13 is a graph showing the relationship between ΔL and the heater power for Example 2.

In the graphs of FIGS. 12 and 13, the x-axis represents the values for $\Delta L$. The y-axis represents the heater temperature and heater power measured in the manner described earlier. When $\Delta L$ is zero, the center of the heat-generating part is at the same position as the center between the openings. When the center of the heat-generating part is closer to the proximal end of the sensing element than the center of the openings the value of $\Delta L$ is negative, and when it is closer to the distal end of the sensing element the value of $\Delta L$ is positive. For this measurement, the ratio $L_1/L_2$ of the oxygen concentration detector was kept at 1.1.

The same graphs show that the heater temperature and heater power are lowest when $\Delta L=0$, i.e. the centers of the heat-generating part and between the openings are at the same position, and the greater the shift in position, the greater the increase in the heater temperature and heater power. When $\Delta L$ is greater than $L_2/4$ and $-L_2/4$, the heater temperature and heater power rise above 1050° C. and 25 W, respectively.

Thus, by setting the conditions so as to satisfy $L_1/L_2 = 0.9$–$1.3$ and $\Delta L < L_2/4$, it is possible for the heater to heat the sensing element to the activation temperature more rapidly, without raising the heater temperature above the heat-resistant temperature of the heater and without resulting in poor efficiency of the heater power.

In addition, it becomes possible to supply the power necessary to raise the temperature of the heater with the voltage from a battery as described above.

Example 3

Figure 14:
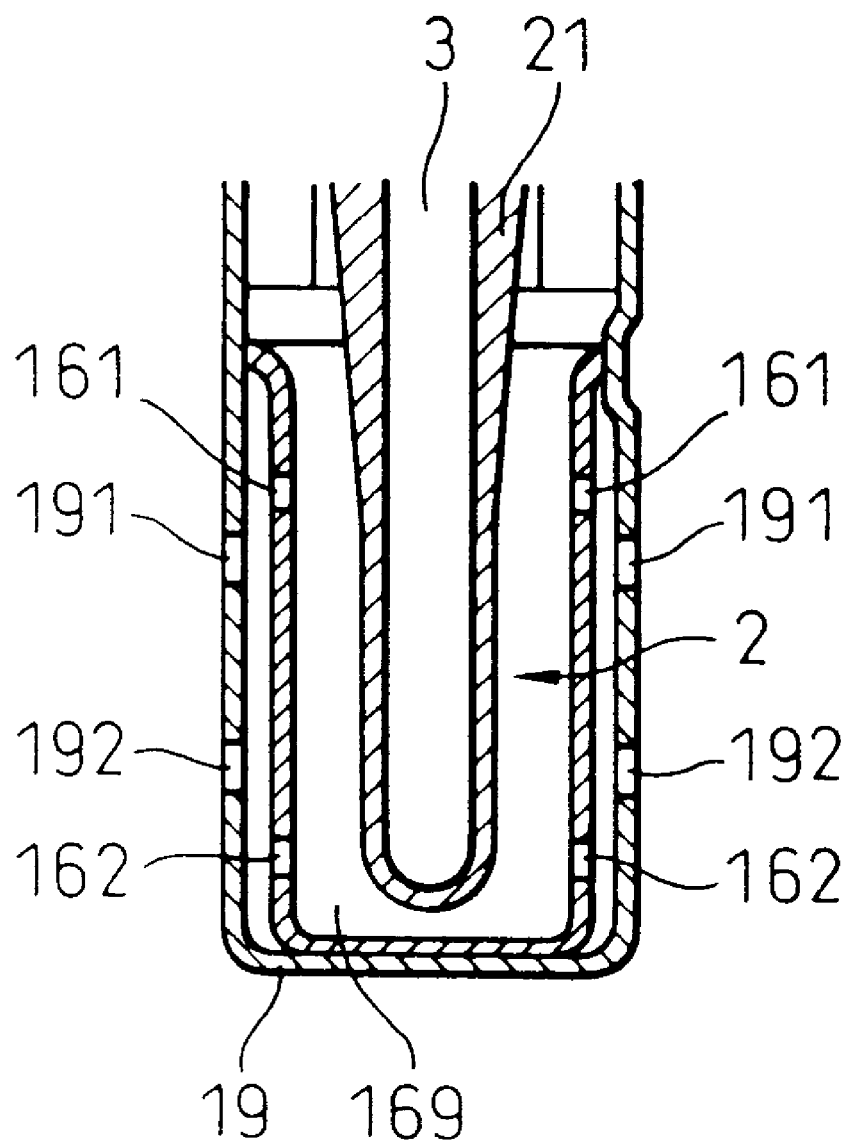
FIG. 14 is an abbreviated illustration of the sensing element and protecting cover of Example 3.

This embodiment, shown in FIG. 14, is an oxygen concentration detector provided with an external cover 19 which has throughholes on the outside of the protecting cover 16.

The external cover 19 is fixed at the bottom of the housing together with the protecting cover 16, and this external cover 19 is provided with upper and lower levels of throughholes 191, 192. Also, the throughholes 191 and 192 are positioned so as not to face the openings 161 and 162, respectively.

The other parts are the same as in Example 1.

Incidentally, contamination is included in the gas to be measured which contacts directly with the sensing element 2, and the contamination inflicts damage on the sensing element 2.

In addition, depending on the location of the oxygen concentration detector, water droplets infiltrating through the openings 161, 162, etc. can cause cracks in the sensing element 2.

For these reasons, the oxygen concentration detector of this embodiment is provided with the external cover 19 on the outside of the protecting cover 16, and is situated so that the throughholes 191, 192 do not face the openings 161, 162, to provide even greater protection of the sensing element 2 against such substances.

Example 4

In this example, as shown in FIGS. 15A to 18, there are illustrated various different heaters, and their heat-generating parts, for oxygen concentration detectors.

Figure 15C:
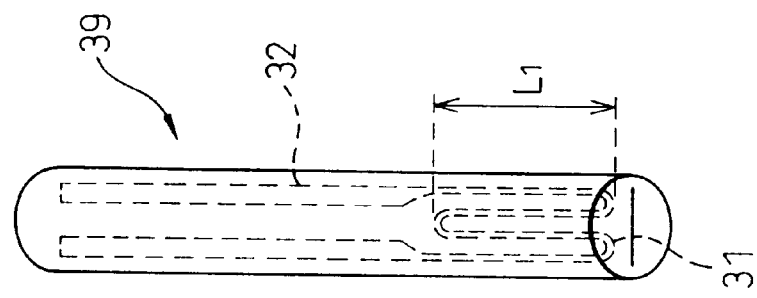
FIGS. 15A to 15C are structural views of the heater of Example 4.
Figure 15B:
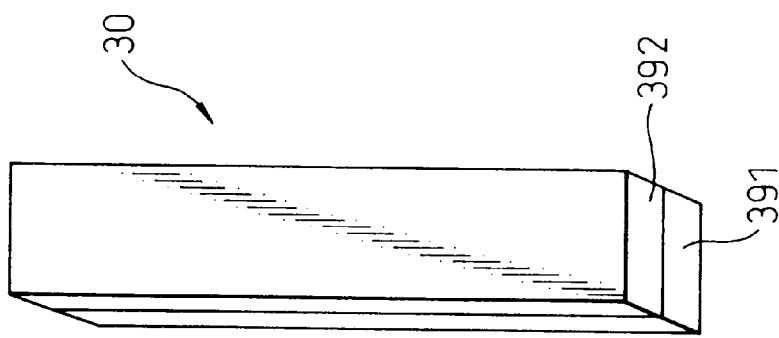
Figure 15A:
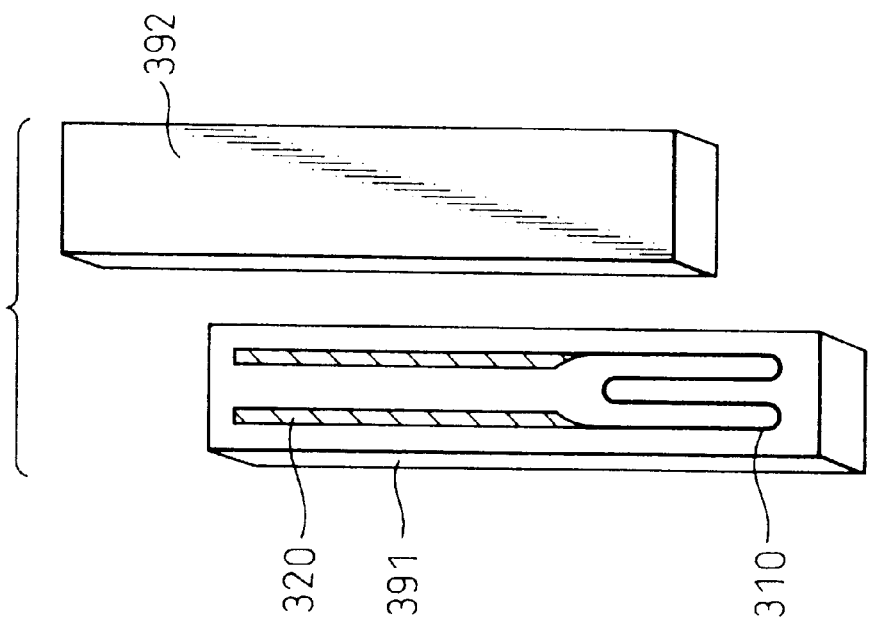
Figure 17A:
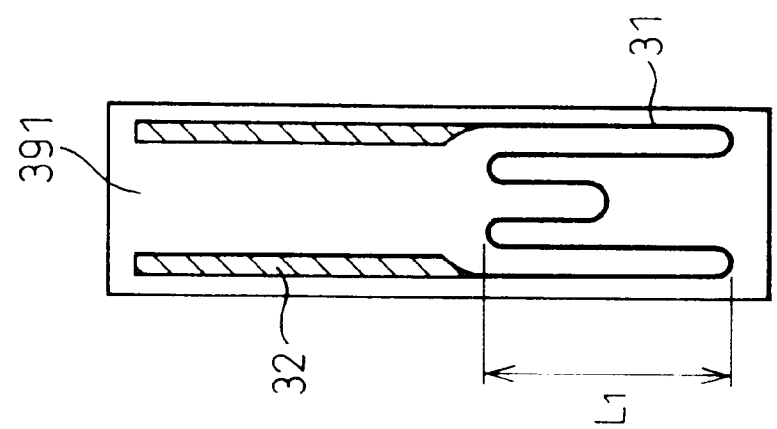
FIGS. 17A to 17C illustrate different heat-generating parts for Example 4.
Figure 17B:
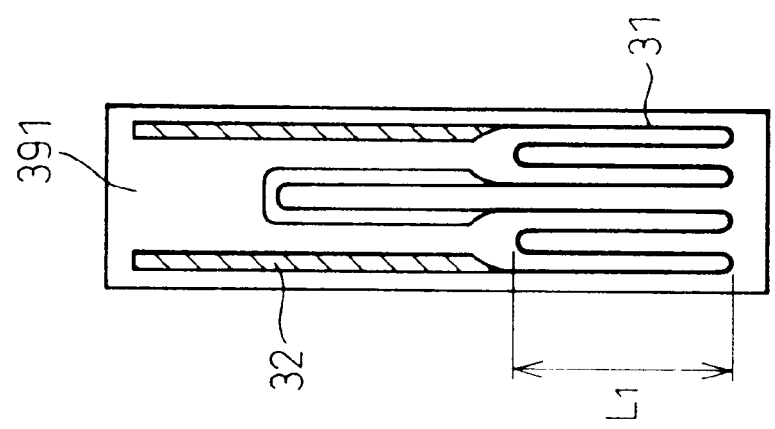
Figure 17C:
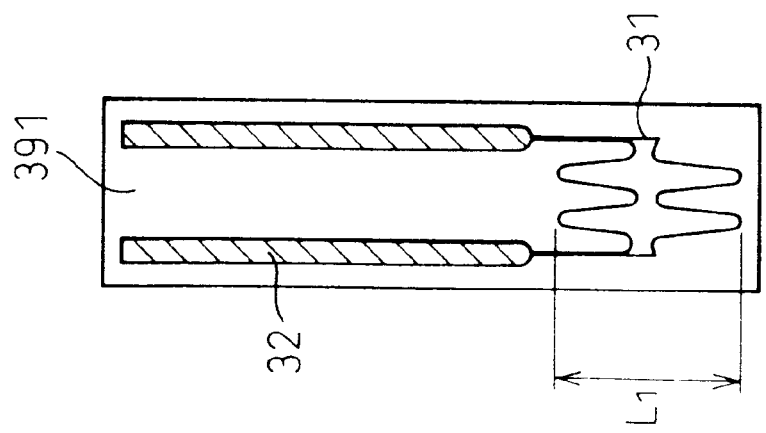

FIGS. 15A to 15C show a heater 39 with an internal heat-generating part 31 and lead part 32.

In order to produce the above-mentioned heater 3, a tungsten paste is first printed on an unbaked ceramic board 391 in the pattern shown in FIG. 15A, and then a ceramic board 392 of the same shape is placed over it to make a ceramic body 30, as shown in FIGS. 15A and 15B.

This ceramic body 30 is then baked, and finally cut and worked into a rod shape to obtain a cylindrical heater 39, as shown in FIG. 15C.

In FIG. 15C, $L_1$ is the length of the heat-generating part 31.

FIGS. 16A to 16C and FIGS. 17A to 17C show shapes of the tungsten paste printed in unbaked ceramic sheets or ceramic boards 391 in the same manner, with the heater 3 of Example 1 or the heater 39 shown in FIG. 15.

The tungsten paste comprises a patterned section formed into a narrow, intricate shape which is to be the heat-generating part 31 after baking, and a wide section which is to become the lead part 32 after baking. The lengths $L_1$ in FIGS. 16A to 16C and FIGS. 17A to 17C are the lengths of the heat-generating part 31.

Figure 18:
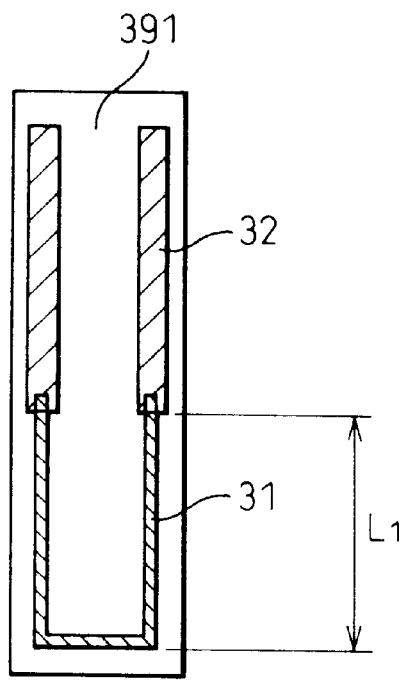
FIG. 18 illustrates a heat-generating part for Example 4.

FIG. 18 shows a heat-generating part 31 and lead part 32 printed using two types of tungsten paste on an unbaked ceramic sheet or ceramic board 391 with the heater 3 of Example 1 or the heater 39 shown in FIG. 15.

That is, the patterned section which is to become the heat-generating part 31 is constructed using paste with a large resistance temperature coefficient, and the wide section which is to become the lead part 32 is constructed using paste with a small resistance temperature coefficient. The length $L_1$ shown here is also the length of the heat-generating part 31.

The tungsten paste actually contracts slightly upon baking, but in FIGS. 16A to 18 only the lengths after baking are shown. The heaters in FIGS. 16A to 18 are prepared in the same manner as those in FIGS. 15A to 15C.

The length $L_1$ of the heat-generating part may be indicated as in this example even when the heat-generating part has a shape other than the ones shown here. Most heat-generating parts are made from sections which are more narrow with more complicated shapes, or sections formed from materials with larger resistance temperature coefficients.

Example 5

An extra opening level is provided in the protecting cover as shown in FIG. 19.

Example 6

Figure 20:
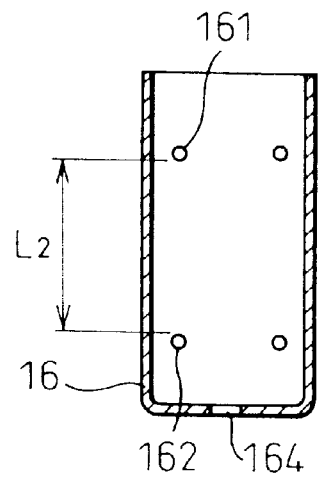
FIG. 20 illustrates a protecting cover for Example 5.

An opening is provided in the bottom of the protecting cover as shown in FIG. 20. By this cover, the responsibility of the sensor can be improved.

Example 7

The construction of the detecting element is not limited to the construction described above.

Figure 21:
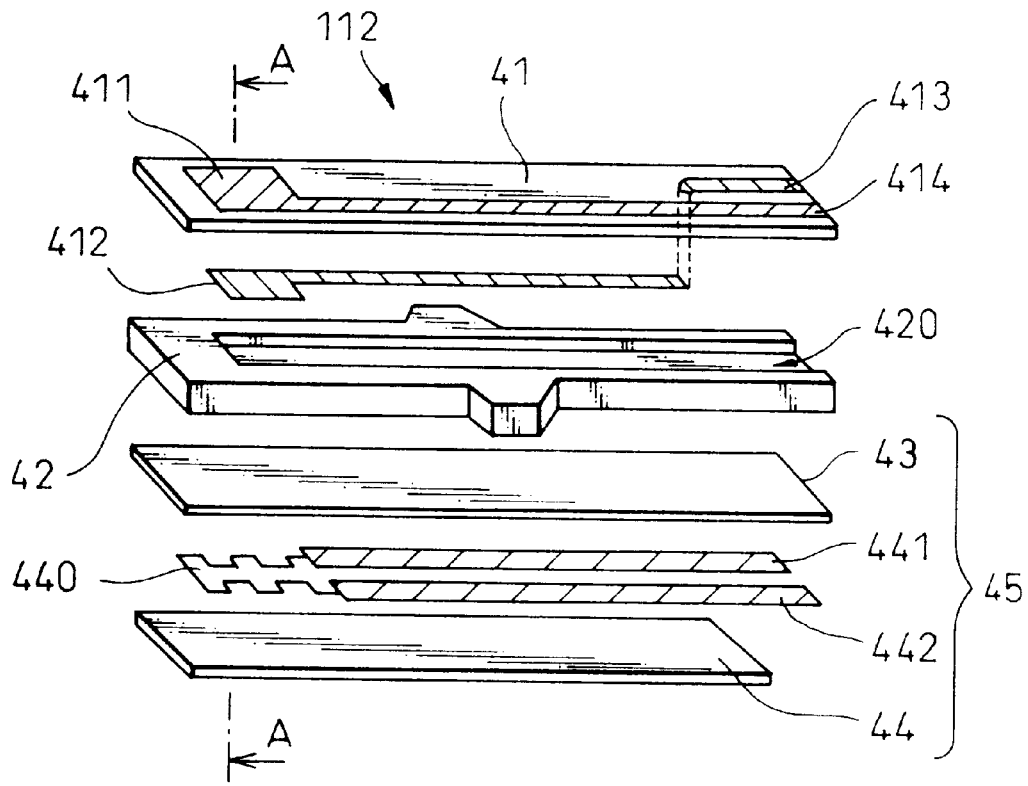
FIGS. 21 and 22 illustrate a laminate type sensing element.
Figure 22:
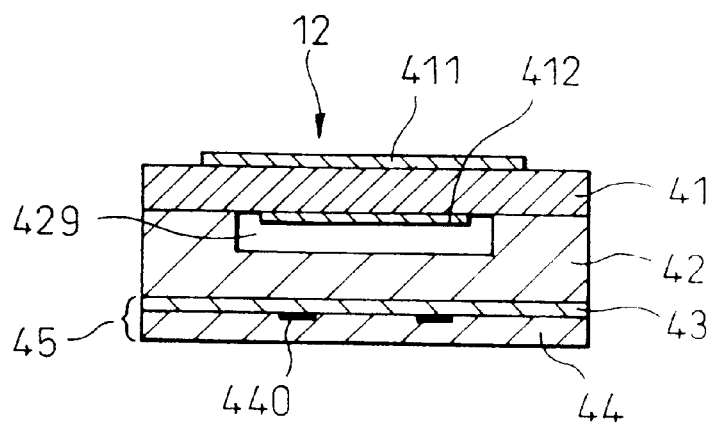

As shown in FIGS. 21 and 22, the sensing element 112 described above can be a laminate type sensing element 112 having a flange portion on the side surface thereof.

The sensing element 112 comprises a sheet-like solid electrolyte 41 and an alumina substrate 42 laminated with the solid electrolyte 41. The solid electrolyte 41 and a groove portion 420 formed on the alumina substrate 42 together define a reference gas chamber 429.

A gas-to-be-measured side electrode 411 is disposed on one of the surfaces of the solid electrolyte 41 and a reference gas side electrode 412 is disposed on the other. Lead portions 413 and 414 are provided to the gas-to-be-measured side electrode 411 and the reference gas side electrode 412, respectively, and the output of the sensing element 12 can be taken out through the lead portions 413, 414 (not shown in the drawing).

A heater portion 45 is disposed on the surface opposite to the surface on which the groove portion 420 is disposed. The heater portion 45 comprises a heat generation member 440 and lead portions 441 and 442 that are bonded to the alumina substrate 43 by a tungsten paste, and an insulating cover 44 covering the upper portion of the heat generation member 440 and the lead portions 441, 442. By the way, the lead portions 441, 442 are connected to a current feed line to the heat generation member 440.

What is claimed is:

1. An oxygen concentration detector comprising:
    a) an oxygen concentration sensing element comprised of a solid electrolyte and an outer electrode provided on the external surface of said solid electrolyte for contributing to detecting the concentration of oxygen in a gas to be measured;
    b) a heater disposed near said solid electrolyte for heating said solid electrolyte said outer electrode being located within the range defined by the length of the heat-generating part of said heater, in the direction of the length of said sensing element; and
    c) a protecting cover separated from said sensing element and extending to cover its exterior for protecting said sensing element, said protecting cover having a first level and a second level of multiple openings in the lengthwise direction, said first and second levels of multiple openings being located outside of the range corresponding to said outer electrode in the direction of the length of said sensing element, there being no openings in said protecting cover in the range corresponding to said outer electrode, said first level of openings being openings which are nearest to an end of said outer electrode and said second level of openings being openings which are nearest to the opposite end of said outer electrode;
    wherein the relationship between the length $L_1$ of said heat-generating part and the distance $L_2$, in the direction of the length of said sensing element, between the edge, on the side of the openings of the second level, of the openings of said first level and the edge, on the side of the openings of the first levels of the openings of the second level, is such that $0.9 \leq L_1/L_2 \leq 1.3$ is satisfied.

2. An oxygen concentration detector according to claim 1, wherein the center position of the heat-generating part of said heater in the lengthwise direction of said sensing element and the center position of said distance $L_2$ have a difference $\Delta L$ in said lengthwise direction of no more than $L_2/4$.

3. An oxygen concentration detector according to claim 1, wherein the area of each individual opening of said two levels of openings is between 0.75 and 3.5 mm$^2$, and the total area of said two levels of openings is between 10 and 23 mm$^2$.

4. An oxygen concentration detector according to claim 1, wherein said outer electrode of said sensing element is formed in the form of a band around the surface of said solid electrolyte, and said openings of said protecting cover do not face said band-form outer electrode.

5. An oxygen concentration detector according to claim 1, wherein a gas diffusion-resistant layer is provided on the surface of said outer electrode of said sensing element.

6. An oxygen concentration detector according to claim 1, wherein an external cover is provided on the exterior of said protecting cover, and said external cover has throughholes.

7. An oxygen concentration detector according to claim 1, wherein said distance $L_2$ is between 9 and 16 mm.

8. An oxygen concentration detector according to claim 1, wherein the length of said heat-generating part of said heater is between 8 and 16 mm.

9. An oxygen concentration detector according to claim 1, wherein said protecting cover has an opening at its bottom.

10. An oxygen concentration detector according to claim 1, wherein said sensing element is a laminate.

11. An oxygen concentration detector according to claim 1, wherein said sensing element comprises a closed end cylindrical solid electrolyte.

* * * * *